(12) United States Patent
Pedrazzini

(10) Patent No.: US 9,638,710 B2
(45) Date of Patent: May 2, 2017

(54) LABORATORY AUTOMATION SYSTEM WITH DOUBLE MOTOR TRACTION DEVICE FOR CONVEYOR BELTS

(71) Applicant: Inpeco Holding Ltd., Qormi (MT)

(72) Inventor: Gianandrea Pedrazzini, Paradiso (CH)

(73) Assignee: INPECO HOLDING LTD., Qormi (MT)

( * ) Notice: Subject to any disclaimer, the term of this patent is extended or adjusted under 35 U.S.C. 154(b) by 0 days.

(21) Appl. No.: 14/903,735

(22) PCT Filed: Jul. 4, 2014

(86) PCT No.: PCT/EP2014/064380
§ 371 (c)(1),
(2) Date: Jan. 8, 2016

(87) PCT Pub. No.: WO2015/004033
PCT Pub. Date: Jan. 15, 2015

(65) Prior Publication Data
US 2016/0161520 A1    Jun. 9, 2016

(30) Foreign Application Priority Data
Jul. 8, 2013  (IT) .............................. MI2013A1145

(51) Int. Cl.
| | |
|---|---|
| *B65G 15/12* | (2006.01) |
| *B65G 37/00* | (2006.01) |
| *G01N 35/04* | (2006.01) |
| *G01N 35/02* | (2006.01) |
| *B65G 21/20* | (2006.01) |
| *B65G 23/04* | (2006.01) |

(Continued)

(52) U.S. Cl.
CPC ......... *G01N 35/04* (2013.01); *B65G 21/2072* (2013.01); *B65G 23/04* (2013.01); *B65G 23/14* (2013.01); *B65G 43/00* (2013.01); *G01N 35/02* (2013.01); *B65G 15/62* (2013.01); *B65G 2812/02108* (2013.01); *G01N 2035/0475* (2013.01)

(58) Field of Classification Search
CPC .................................................. B65G 21/2072
USPC ........................... 198/571, 575, 817; 700/28
See application file for complete search history.

(56) References Cited

U.S. PATENT DOCUMENTS

| | | |
|---|---|---|
| 5,587,915 A | 12/1996 | Nagatomi |
| 9,242,633 B2 * | 1/2016 | Forslow .................... B60K 6/28 |
| 2010/0300831 A1 | 12/2010 | Pedrazzini |

FOREIGN PATENT DOCUMENTS

| | | |
|---|---|---|
| CA | 2126706 | 12/1995 |
| DE | 195 08 492 | 9/1996 |

(Continued)

OTHER PUBLICATIONS

International Search Report dated Sep. 18, 2014.

*Primary Examiner* — Gene Crawford
*Assistant Examiner* — Lester Rushin
(74) *Attorney, Agent, or Firm* — Jacobson Holman, PLLC.

(57) ABSTRACT

A laboratory automation system is described, comprising pairs of conveyor belts accommodating devices for conveying biological samples and actuated by a motorized traction device. Said motorized traction device includes a first and a second motor, each adapted to actuate both said pairs of belts a central control unit being adapted to control the simultaneous or alternating actuation of said motors.

5 Claims, 6 Drawing Sheets

(51) Int. Cl.
*B65G 23/14* (2006.01)
*B65G 43/00* (2006.01)
*B65G 15/62* (2006.01)

(56) References Cited

FOREIGN PATENT DOCUMENTS

| | | | |
|---|---|---|---|
| DE | 19508492 A1 * | 9/1996 | ............. B65G 23/36 |
| DE | 200 22 495 | 12/2001 | |
| EP | 2 225 567 | 9/2010 | |
| EP | 2 377 786 | 10/2011 | |
| WO | 2009/068555 | 6/2009 | |
| WO | 2015/004033 | 1/2015 | |

* cited by examiner

LABORATORY AUTOMATION SYSTEM WITH DOUBLE MOTOR TRACTION DEVICE FOR CONVEYOR BELTS

The present invention relates to a laboratory automation system with double motor traction device for conveyor belts.

BACKGROUND OF THE INVENTION

In the field of conveying biological material specimens in a test laboratory it is known to use appropriate automation systems adapted for the purpose which allow the specimens, appropriately contained in test tubes, to interface with the pre- and post-testing modules and with the proper testing modules adjacent to the automation system itself.

In particular, the test tubes, each of which is inserted into a conveying device, travel along motorized conveyor belts which substantially form specimen dispatching lanes along the automation system, as described by the Applicant in patent EP-2225567.

Due to the size of a test laboratory and thus to the corresponding automated specimen conveying system, the above-described conveyor belts may naturally reach even considerable lengths, up to several tens of meters.

As mentioned, said belts are motorized, and at each rectilinear portion of the automation system there are two motors, at the opposite ends, each of which manages the actuation of one of the two pairs of belts (outbound lanes and return lanes).

The drivers of the belts, during their normal operation, are certainly subject to considerable stress; since test laboratories typically work non-stop all day, seven days a week, the motors which actuate the conveyor belts are always operating and this increases the risk of their deterioration and even failure. In particular, this concerns ratio motors which deteriorate due to the presence of pulsing loads which act on the gears of the ratio motors themselves, thus leading to their failure on the long run.

So, it would be necessary to manually act in order to replace the deteriorated or failed motor, and this would naturally imply the need to interrupt the operation of the automation system or at least of the concerned portion (i.e. that with the belts operated by the motor to be replaced) during such a maintenance operation, with obvious consequences in the form of delays in the specimen treatment procedures.

DE-19508492 describes a conveyor controlled either simultaneously or alternatively by a pair of motors.

BRIEF SUMMARY OF THE INVENTION

It is the object of the present invention to provide a laboratory automation system in which operation continuity is ensured, even in the unfortunate case of problems or failures of the motorized traction system of one of the two pairs of conveyor belts.

This and other objects are achieved by a laboratory automation system as described in claim 1.

BRIEF DESCRIPTION OF THE SEVERAL VIEWS OF THE DRAWINGS

These and other features of the present invention will become further apparent from the following detailed description of an embodiment thereof, shown by way of non-limiting example in the accompanying drawings, in which.

DETAILED DESCRIPTION OF THE INVENTION

Figure 1:
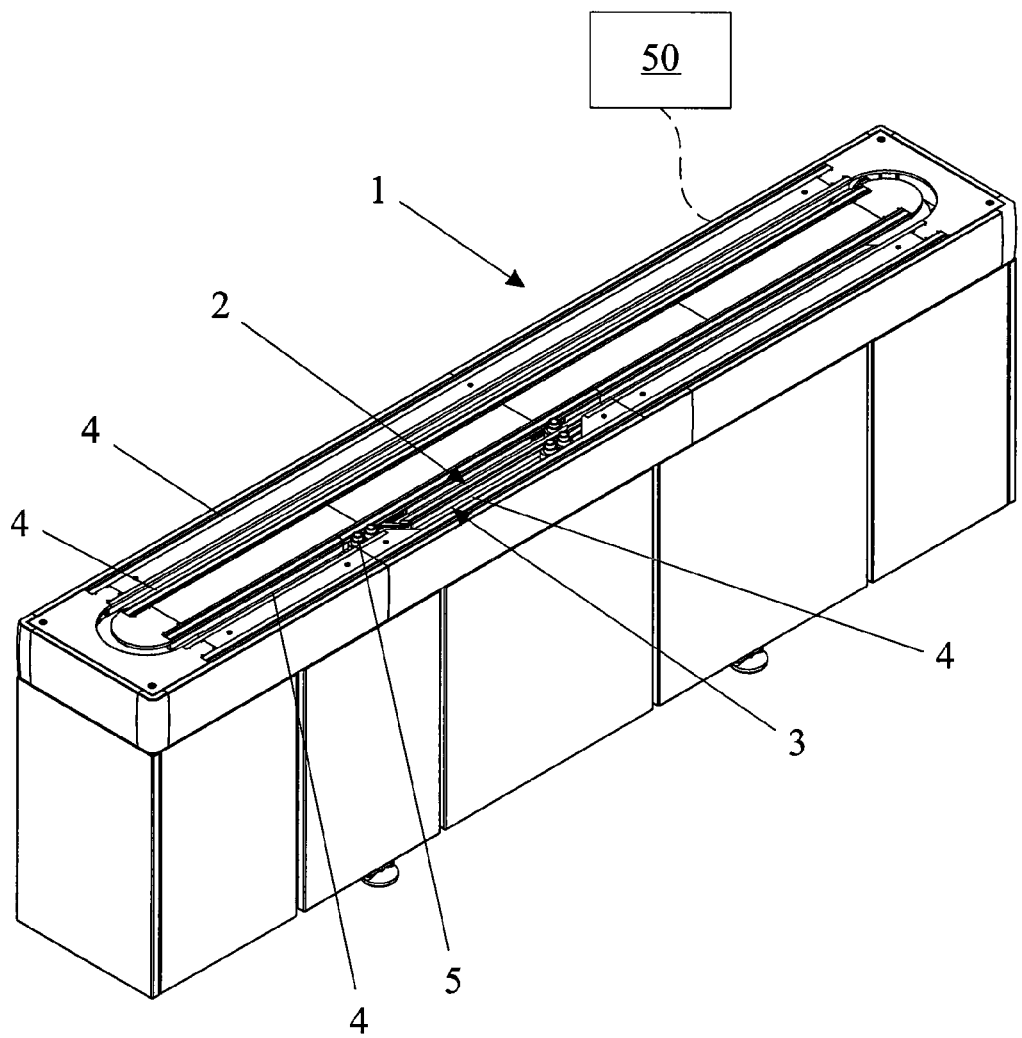
FIG. 1 shows a perspective view of a portion of the laboratory automation system.

A laboratory automation system comprises main lanes 2 and secondary lanes 3 parallel to one another (FIGS. 1, 2) which accommodate parallel, motorized conveyor belts 4 made of polyurethane, having the function of conveying test tube conveying devices 5.

The conveying devices 5 are usually diverted onto the secondary lane 3 to allow them to reach or pass pretesting, testing or post-testing modules or stations.

The system consists of modules 1 (FIG. 1) assembled together in a variable number and according to different configurations to respond to the various test laboratory needs.

One pair of belts 4, sliding in one direction, and one pair of belts 4, sliding in the opposite direction, are present for each rectilinear stretch of the system (angular and T-shaped connections are also provided, if needed; in this regard see patent EP-2225567 by the Applicant).

Figure 2:
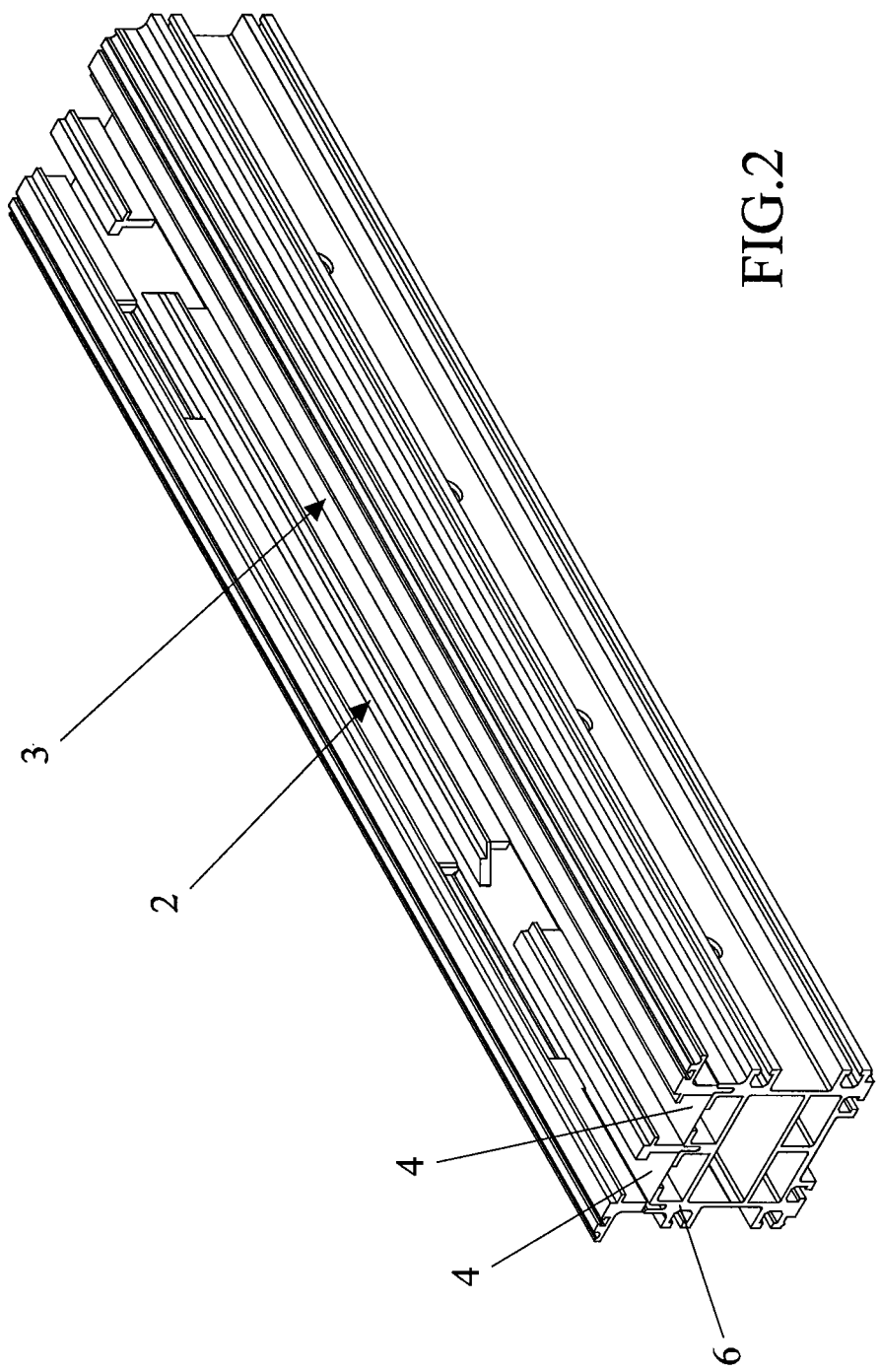
FIG. 2 shows a perspective view of a sliding profile of a pair of conveyor belts of the automation system.

Each pair of lanes 2, 3 is obtained from a sliding profile 6 of belt 4, appropriately shaped and advantageously made of aluminum (FIG. 2).

Each belt 4 is made of cross-linking polyurethane coated with impregnated fabric which ensures a low friction coefficient with the resting surface of the conveying device 5 during the movement.

At each conveying end of the automation system, in order to allow the conveying device 5 to invert the movement direction, there is a motion inversion device 11 (FIGS. 3, 6, 7), comprising a thin plastic disc 110, having the function of transferring each conveying device 5 transiting from the pair of belts 4 sliding in one direction to the pair of belts 4 sliding in the opposite direction.

A traction device 100 of the pair of conveyor belts 4 is provided again at the end of the automation system (FIGS. 3-7). It comprises a first motor 111a which rotates a first pulley 112a (FIG. 4) on which a first belt 113 is wound, the other end of which is wound about a third pulley 112c.

The rotation of such a third pulley 112c is transmitted to a rubber-coated roller 115 (FIGS. 3, 6) which by rotating generates the movement of the pair of belts 4 which are wound about it (for conveniently viewing the rubber-coated roller 115, the portion of belts 4 wound about the roller itself has been omitted). At the same time, the rotation of the third pulley 112c actuates a further thin belt 116 (FIGS. 6, 7) which, by resting on some idle pulleys 117a, 117b, 117c (FIG. 6), rotates the plastic disc 110 thus actuating the motion inversion device 11.

Figure 3:
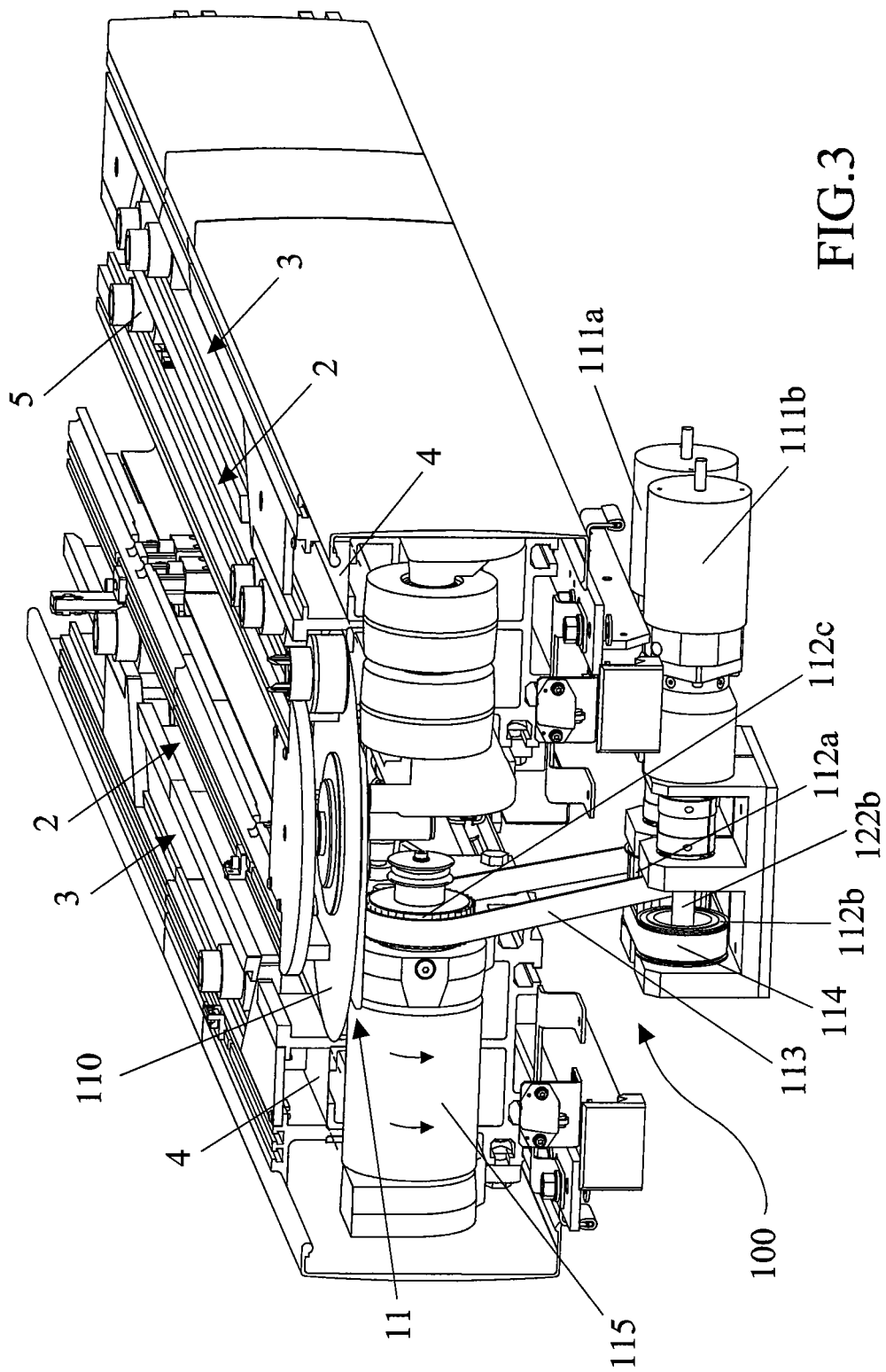
FIG. 3 shows a perspective view of an end of the portion of the automation system.
Figure 4:
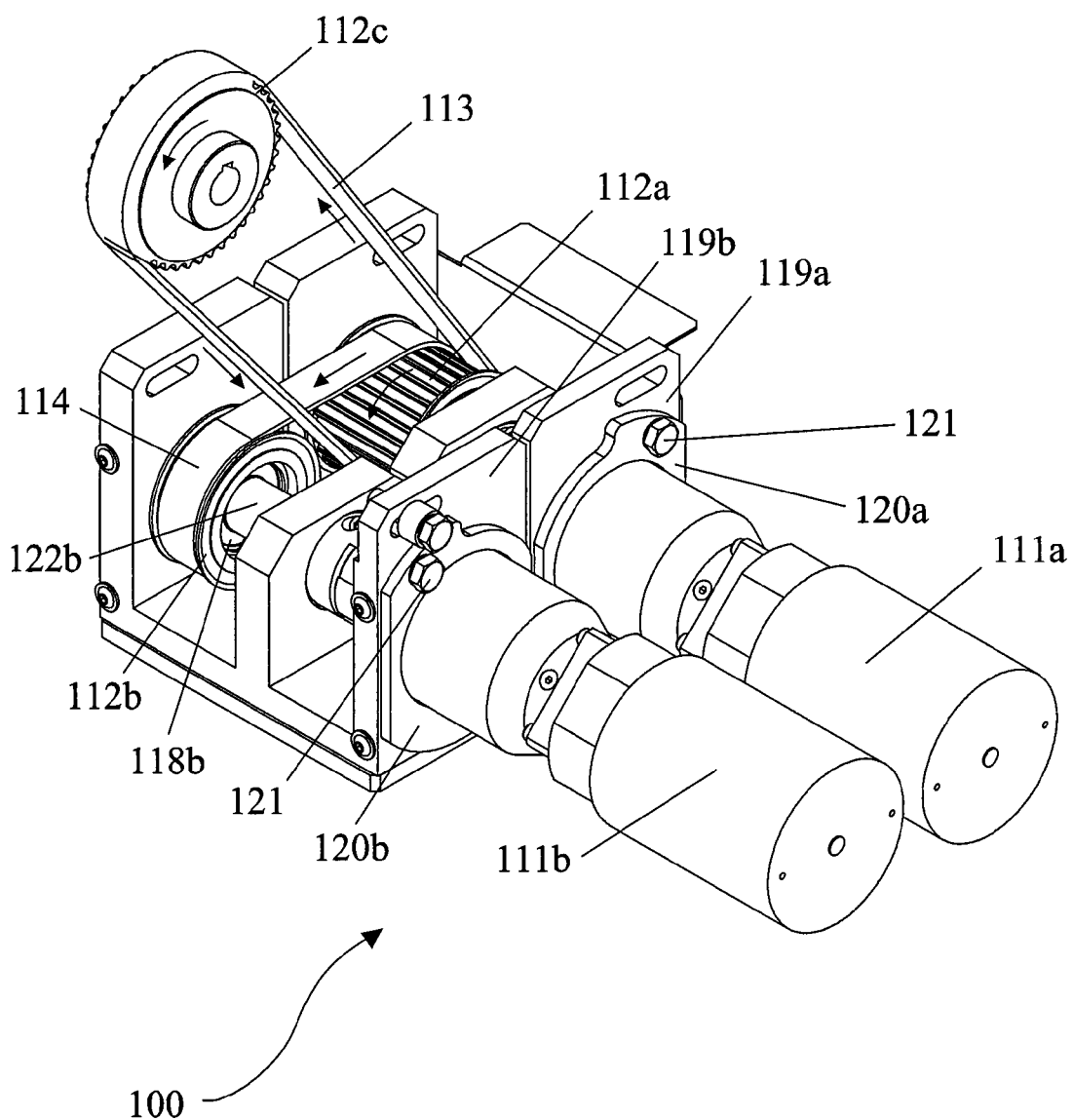
FIG. 4 shows a perspective view of the motorized traction device.

The traction device 100 further comprises a second motor 111b which rotates a second pulley 112b, on which a second belt 114 is wound, which at the other end is wound about the first pulley 112a again (FIGS. 3, 4).

Figure 5:
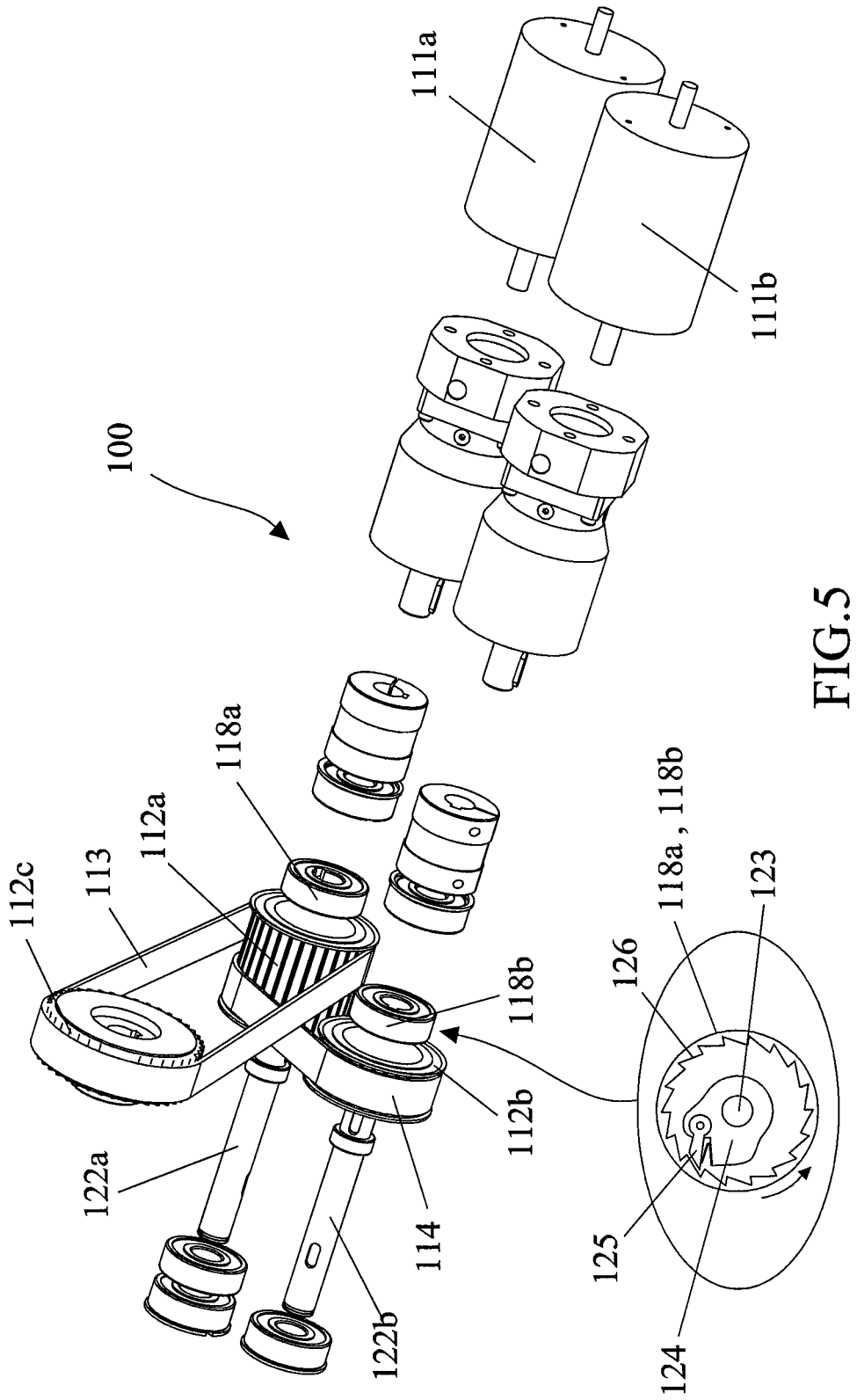
FIG. 5 shows an exploded view of the motorized traction device shown in FIG. 4, comprising a section view perpendicular to the rotation axis of a free wheel mechanism used therein.

The first and second pulleys 112a and 112b accommodate a first and a second free wheel 111a and 118b therein, respectively (FIG. 5, where said free wheels 118 and 118b are shown in detail).

The traction device 100 also comprises two supports 119b (FIGS. 4, 7) for each of the two motors 111a, 111b; each support 119a, 119b has a joint 120a, 120b which, fixed by means of screws 121 to support 119a, 119b, facilitates the possible maintenance operations on the motors, as will be described in greater detail below.

During the normal operation of the traction device 100 of the conveyor belts 4 of a laboratory automation system, only the first motor 111a is working; a rotation movement is thus imposed on the corresponding shaft 122a which, at a region 123, is integral with a hub 124 (see detail in FIG. 5) and with a ratchet 125. When the shaft 122a is actuated, ratchet 126 engages the teeth of the first free wheel 118a, which rotates (counterclockwise in the embodiment), thus exerting a feeding effect on pulley 112a. As a result, the first belt 113 also slides and the third pulley 112 rotates (see the arrows in FIG. 4).

Figure 6:
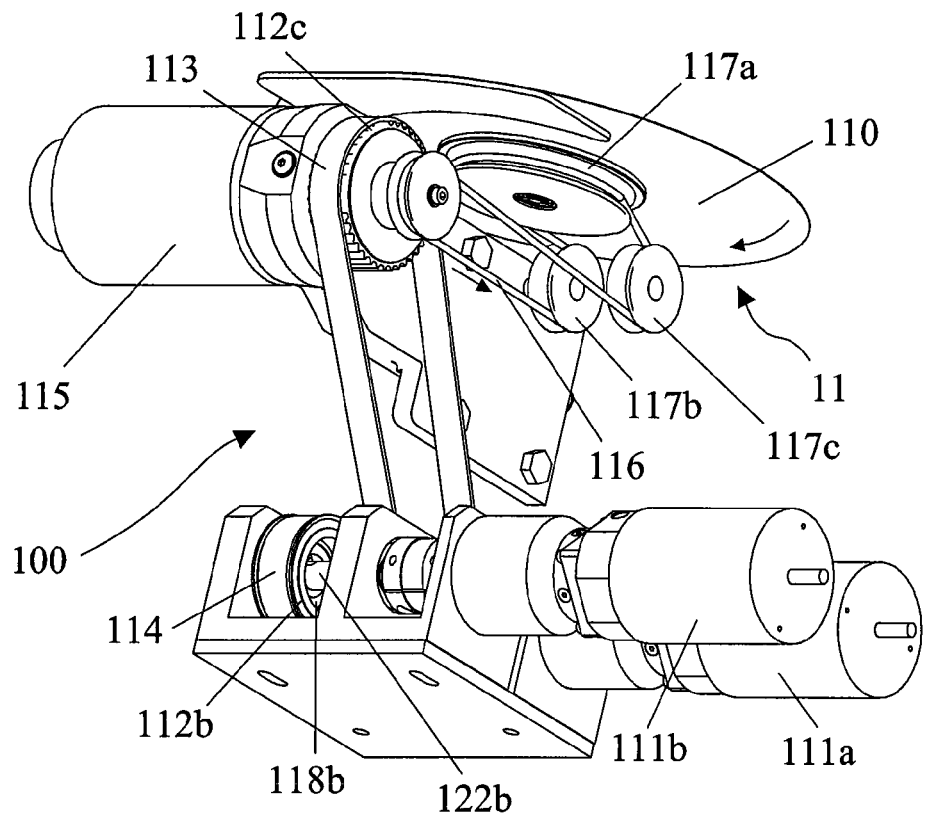
FIGS. 6 and 7 show the motorized traction device again, in a bottom and a side view, respectively.
Figure 7:
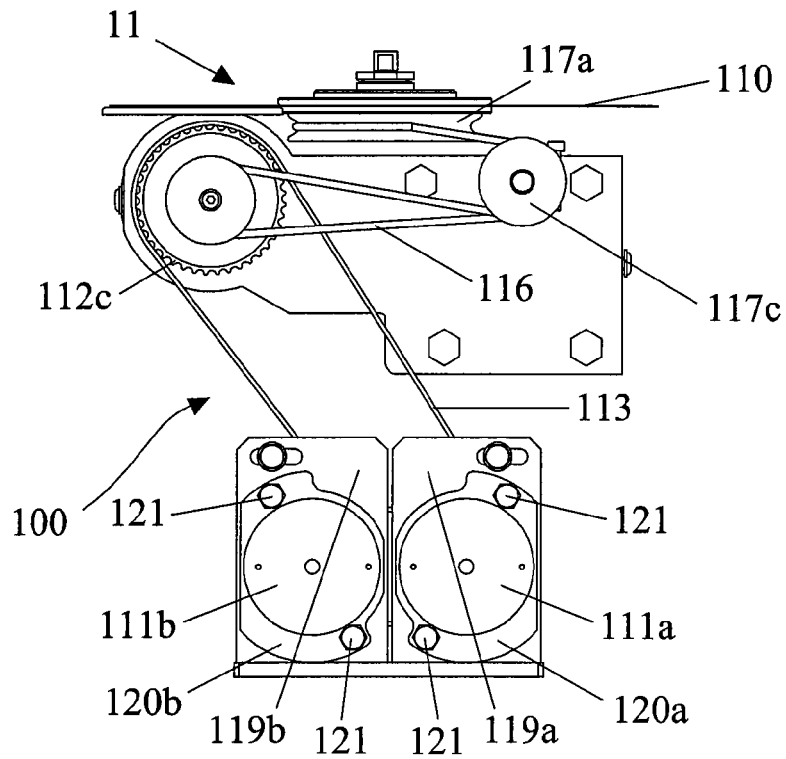

The latter rotation causes, in turn, the rotation of the rubber-coated roller 115 (FIG. 3), and thus the sliding movement of the conveyor belts 4, as mentioned only partially shown in FIG. 3 for viewing the rubber-coated roller 115 (note the dashed line of the belts 4). Furthermore, the rotation of the third pulley 112c again causes the sliding movement of belt 116 which by winding on the idle pulley 117c causes the rotation thereof, thus causing in turn the plastic disc 110 to rotate (FIGS. 6, 7).

It is thus apparent that the action of the first motor 111a, resulting in the sliding movement of the conveyor belts 4 and in the rotation of the plastic disc 110, allows a conveying device 5 which is reaching the end of belt 4 (i.e. the header of the module 1 of the automation system) to be routed to the conveyor belt 4 which is sliding parallel in the opposite direction, the latter being operated, in turn, by the respective pulley (not shown in FIG. 3) at the other end of the module 1 of the system. Thereby, the conveying device 5 switches from the outbound lane (or pair of lanes) to the return lane(s) and vice versa at the other end.

Obviously, the rotation of the first pulley 112a also slides the second belt (FIG. 4) and thus rotates the second pulley 112b. A counterclockwise rotation is again imposed on the second free wheel 118b inside the second pulley 112b. In all cases, it is apparent that only the toothed profile 126 of the second free wheel 118b rotates, which slides on the ratchet 125 thereof, which is stationary as hub 124 and shaft 122b (since the second motor 111b is not operating). So, in this step, only the second free wheel 118b is indeed "free", i.e. does not exert any traction but only a simple bearing function inside pulley 112b.

As time goes by, the first motor 111a may show wear, even more if considering that the motor is used in automation systems which are never stopped.

The second motor 111b is indeed delegated to take over as "spare" traction device of belts 4, when the first motor 111a is about to reach the end of its life cycle.

The operating logic is managed by a central control unit 50 of the automation system (conveniently shown only with reference to module 1) capable of discriminating the occurrence of faulty operation of the first motor 111 and of automatically switching the task of feeding belts 4 to the second motor 111b.

This occurs by appropriately controlling each of the software drivers associated with the two motors so as to stop the first motor 111a and start the second motor 111b at the same time.

Such a switching occurs mandatorily in the case of sudden failure of the first motor 111a, but may also occur according to a more complex mechanism which takes into account, for example, the exceeding of given threshold values for specific parameters of the motor which are configurable so as to trigger proper warnings at the level of the central control unit 50.

For example, a maximum current value through the motor may be established, which results in a maximum value of power which may be drawn by the driver of the motor itself. Alternatively, the maximum life of a motor may be considered as a key parameter.

In such cases, the activation of a warning may not have the immediate switching between the two motors as a consequence; indeed, a possible decision about this topic is also processed according to a predictive logic implemented in the central control unit 50 and which allows to process data and information related to the components in hand over time (and thus during the life of a given motor or more generally of an automation system), thus determining which conditions in the past most often caused a definitive failure of the motors.

Thus, the decision to switch from one motor to the other or not may be taken by the central control unit 50, taking into account both the possibly exceeded thresholds (or the limit life time of a motor) and such "historical" information on the behavior of the motors. This is obviously aimed at avoiding the situation of complete failure of the operating motor, which would stop the system, and thus at preventively switching to the other motor.

Obviously, the central control unit 50 may also be programmed to start the switching between the two motors in all cases when a given threshold is exceeded, and thus in the presence of a warning signal, similarly to the above-described case of motor failure.

On the long run, the central control unit 50 can autonomously create proper "behavior rules" which allow to operate in a timely manner when any situation occurs.

Therefore, when the above-described situation occurs, the first motor 111a is stopped by the central control unit 50 which also starts the second motor 111b arranged in parallel thereto; the second motor 111b keeps the second pulley 112b rotating and therefore, by means of the second belt 114, the first pulley 112a and again the third pulley 112c by means of the first belt 113.

In this case, in a symmetric manner with respect to the previous situation, it is the second free wheel 118b which, by virtue of the rotation imposed on the shaft 122b of the second motor 111b (FIG. 5) performs a feeding effect on pulley 112b. Instead, it is the first free wheel 118a to be "free" and to exert the bearing action inside pulley 112a, while there no rotation of shaft 122a occurs because the first motor 111a is stationary. Therefore, despite the interruption of the operation of the first motor 111a, the feeding continuity of the pair of conveyor belts 4 is certainly still ensured by virtue of the fact that the second motor 111b has taken over from the first.

In the meantime, while the automation system continues to operate without problems by virtue of the second motor 111b, the central control unit 50 outputs an appropriate notification (which may be displayed, for example, on a graphic user interface connected to the automation system) by virtue of which an operator becomes aware of the switching and can thus replace the first motor 111, which has just stopped working, in a very practical manner; in particular, the operator may unscrew the screws 121 and thus remove the first motor 111 from the support 119*a* and replace it with a new one, and this occurs while the newly started second motor 111*b* is working normally.

After the replacement, the operator manually resets the notification concerning the motor to be changed on the GUI.

An alternative embodiment may certainly be considered, in which the two motors 111 and 111*b* work simultaneously to share the feeding effort of the belts 4.

The innovative aspect of the invention referred to a traction system of a pair of motorized conveyor belts in a laboratory automation system is thus determined by arranging a second motor for traction purposes by the side and parallel to the first.

Such a second motor may automatically take over the first motor, when the latter fails or is expected to be about to fail, thus ensuring operating continuity of the traction system of the concerned pair of conveyor belts, and avoiding the inconvenience related to known solutions consisting in the need to shut down the whole automation system (or at least the part of the system concerned by the failure of the belt traction system) so that an operator can manually replace the single motor present.

Indeed, in the solution of the present patent, the operator can however replace the failed motor but only once the second motor in parallel has been started and is thus keeping the automation system working.

Furthermore, the switching between the two motors is not set by an operator but is controlled at software level by a central control unit, capable of automatically passing, in case of need, the burden of traction of the belts from one motor to the other by means of the smart evaluation of a series of parameters (thresholds, life times) established beforehand and by further applying predictive criteria which result from a historical analysis of the behavior of drivers of the same type in similar systems.

The invention thus described is susceptible to many changes and variants, all within the scope of the inventive concept.

In practice, the materials used as well as the shapes and dimensions may be any, according to needs.

The invention claimed is:

1. A laboratory automation system comprising pairs of conveyor belts accommodating conveying devices of biological samples and actuated by a motorized traction device, wherein said motorized traction device includes a first and a second motor, each adapted to actuate both said pairs of belts, a central control unit being adapted to control the simultaneous or alternating actuation of said motors by means of software drivers associated with each motor, said central control unit being able to discriminate the occurrence of a faulty operation of the first motor and to automatically switch the task of feeding the pairs of belts to the second motor, said switching occurring mandatorily in case of sudden failure of a motor, but also if given threshold values are exceeded for some specific parameters of the motor which are configurable so as to trigger proper warnings at the level of the central control unit before the failure of a motor, said central control unit processing data and information related to said specific parameters over time, determining which conditions in the past most often caused a definitive failure of the motors, thus updating the threshold values according to historical information on the behavior of the motors so as to avoid the situation of complete failure of the operating motor, which would stop the system, and to preventively switch to the other motor accordingly, on the long term, said central control unit autonomously creating proper "behavior rules" which allow it to act in a timely manner if any situation occurs.

2. The system according to claim 1, wherein said motorized traction device comprises a first, a second and a third pulley, said first and second pulley being respectively and selectively connected to each of said first and second motors by means of respective engageable free wheels, a first belt being wound on said first and third pulley and a second belt (114) being wound on said first and second pulley.

3. The system according to claim 2, wherein said engageable free wheels are integral with said first and second pulley, and selectively feedable by respective shafts of said first and second motor.

4. The according to claim 2, wherein said third pulley actuates a further belt which, by resting on idle pulleys, is adapted turn a disc, thus actuating a motion inversion device of conveying devices.

5. The system according to claim 4, wherein said third pulley is connected, by controlling the rotation thereof, to a rubber-coated traction roller of said pair of belts.

* * * * *